United States Patent

Kuhn

[11] Patent Number: 6,161,033
[45] Date of Patent: Dec. 12, 2000

[54] IMAGE GUIDED SURGERY SYSTEM

[75] Inventor: Michael H. Kuhn, Hamburg, Germany

[73] Assignee: U.S. Philips Corporation, New York, N.Y.

[21] Appl. No.: 09/291,433

[22] Filed: Apr. 13, 1999

[30] Foreign Application Priority Data

Apr. 17, 1998 [DE] Germany .......................... 198 17 039

[51] Int. Cl.[7] .................................................. A61B 19/00
[52] U.S. Cl. .......................... 600/429; 606/130; 600/407
[58] Field of Search ........................... 606/130; 600/426, 600/429, 427, 407; 356/375, 152.3, 152.1, 141.1, 141.2, 152.2

[56] References Cited

U.S. PATENT DOCUMENTS

| 5,590,655 | 1/1997 | Hussman | 128/653.1 |
| 5,622,170 | 4/1997 | Schulz | 128/653.1 |
| 5,772,594 | 6/1998 | Barrick | 600/407 |
| 5,848,967 | 12/1998 | Cosman | 600/426 |
| 5,921,992 | 7/1999 | Costales et al. | 606/130 |

FOREIGN PATENT DOCUMENTS

WO 9740763   11/1997   WIPO .......................... A61B 19/00

*Primary Examiner*—Marvin M. Lateef
*Assistant Examiner*—Eleni Mantis Mercader
*Attorney, Agent, or Firm*—John F. Vodopia

[57] ABSTRACT

The invention relates to an image guided surgery system, having an optical position measuring system which includes a detector arrangement (3) and a marker arrangement (4, 5, 6). In known optical position measuring systems, for example comprising two cameras and three LEDs per marker arrangement, a direct line of sight must continuously exist between the detector arrangement (3) and the marker arrangement (4, 5, 6) in order to ensure reliable and continuous operation of the system and to supply the surgeon continuously with information concerning the current position of an instrument or another part provided with a marker arrangement during the treatment. Blocking of the direct line of sight has a negative effect on the operation of the position measuring system. These drawbacks are avoided according to the invention in that at least one mirror (7) is provided in order to establish an indirect line of sight (5i, 6i) between the detector arrangement (3) and the marker arrangement (4, 5, 6). It is thus ensured that at least one line of sight exists at all times.

6 Claims, 1 Drawing Sheet

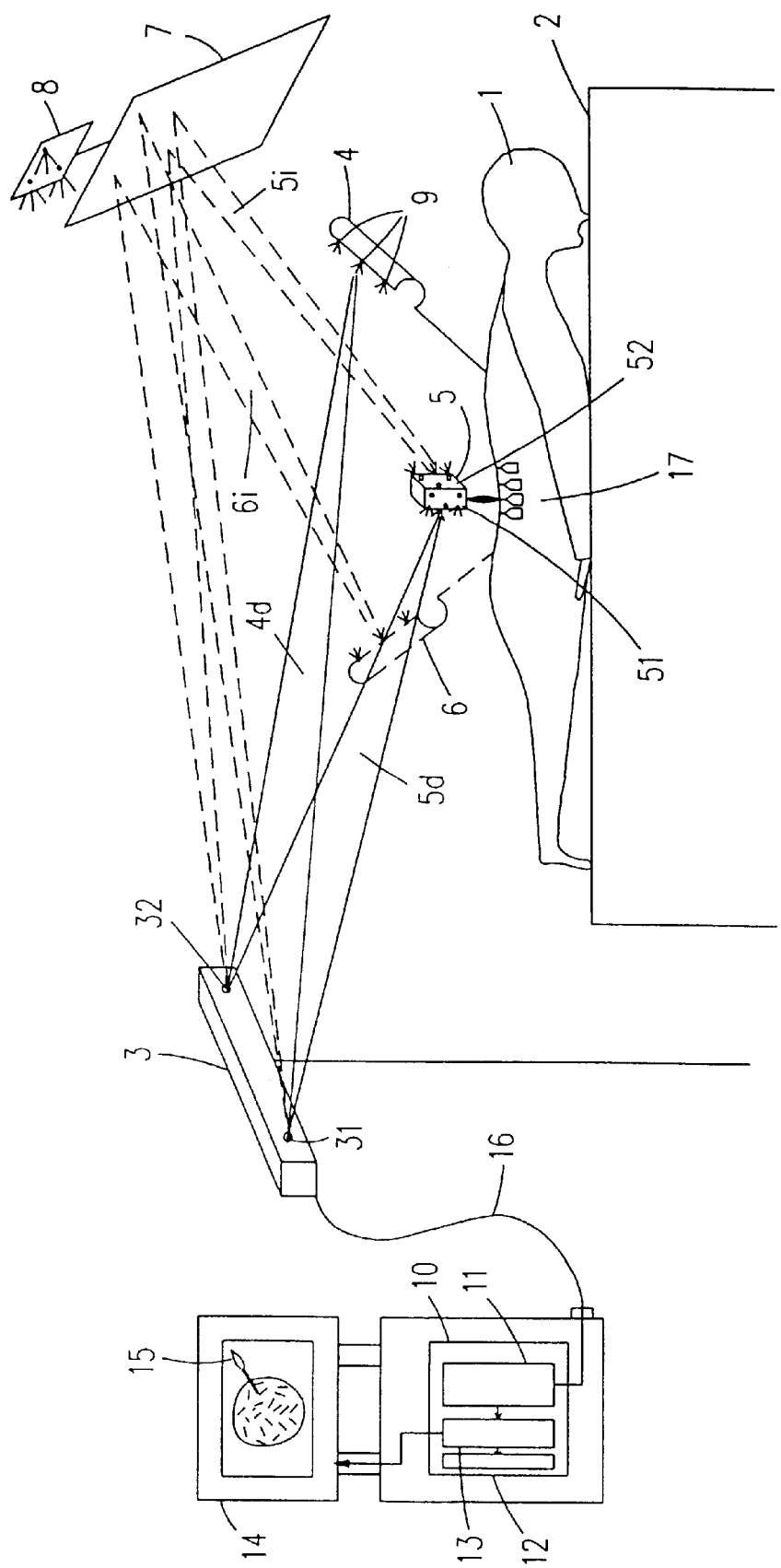

IMAGE GUIDED SURGERY SYSTEM

BACKGROUND OF THE INVENTION

1. The invention relates to an image guided surgery system, comprising a position measuring system which includes a detector arrangement and a marker arrangement.

2. Description of Related Art

A system of this kind is described in WO-A1-97/40763. Two cameras, capable of detecting visible light or infrared light, are mounted on a stand so as to be immobile in space. An instrument for treatment is provided with diodes which emit light that can be detected by the cameras. Using the cameras, the position of the instrument can be determined in a co-ordinate system coupled to the cameras. This position can be converted into an image position by means of a predetermined transformation matrix, the image having been acquired in advance, for example by means of computer tomography (CT) or magnetic resonance tomography (MR). In order to determine said transformation matrix for converting camera co-ordinates into image co-ordinates, markers are provided on the patient during the image acquisition, said markers also being reproduced so as to be visible in the image. Subsequently, the markers are approached by the instrument provided with diodes or by a separate indicator instrument provided with diodes, so that the position thereof is detected in camera co-ordinates. The necessary link between camera co-ordinates and image co-ordinates is thus established and the position of the instrument during a treatment can be indicated in the image.

A position measuring system of this kind is preferably used in neurosurgery so as to show the surgeon the current position of the instrument in the brain of the patient being treated in the image. However, it is a drawback of the known system that the direct line of sight between the detector arrangement (the cameras) and the marker arrangement (the LEDs) may not be blocked, for example by attending staff or other apparatus, in order to ensure continuous and correct operation of the position measuring system.

SUMMARY OF THE INVENTION

Therefore, it is an object of the invention to improve the described system in this respect.

This object is achieved according to the invention in that a mirror is provided in order to establish an indirect line of sight between the detector arrangement and the marker arrangement. It is thus achieved that at any instant at least one line of sight exists and that the current position of the marker arrangement is known at any instant. The mirror can be arranged so as to be stationary relative to the detector arrangement, for example it may be rigidly connected to the detector arrangement or rigidly to the ceiling, but it may also be slidable and adjustable. In order to ensure very accurate position determination also in the case of such a flexible mirror arrangement, when only an indirect line of sight exists between the marker arrangement and the detector arrangement, via the mirror, a marker arrangement is preferably provided also on the mirror in order to determine the position and the orientation of the mirror.

In an advantageous embodiment contributing to an increased operating reliability the marker arrangement comprises a plurality of markers which are arranged in such a manner that a direct as well as an indirect line of sight exists to the detector arrangement. Preferably, the marker arrangement is designed so that an adequate number of markers can always be recognized from any viewing direction, thus enabling reliable and accurate determination of their position.

A further embodiment of the invention is provided with means for associating a detected position with a marker arrangement. These means may consist, for example in that the markers differ (transmit at different frequencies, transmit for periods of unequal length, or are differently arranged from a geometrical point of view) and/or can be operated successively in time.

BRIEF DESCRIPTION OF THE DRAWING

The invention will be described in detail hereinafter with reference to the FIGURE.

DETAILED DESCRIPTION OF THE PREFERRED EMBODIMENT

The patient 1 to be treated is arranged on a patient table 2, a marker arrangement 5 being provided on a vertebra 17 of the patient 1. A camera arrangement 3, constituting the detector arrangement and comprising two CCD cameras 31, 32, is mounted on a stand which is positioned adjacent the patient table 2. Also shown is a surgical instrument 4 which is provided with three markers 9 (light-emitting diodes emitting visible light or infrared light). A direct line of sight 4d exists between the cameras 31, 32 and the LEDs 9 of the surgical instrument 4, so that the position in space of the LEDs 9 can be determined and therefrom the position in space of the surgical instrument 4 can be determined; for this purpose, the detector arrangement 3 is provided with a suitable electronic system for the stereoscopic measurement of light point sources in space. To this end the LEDs 9 are suitably driven, for example in such a manner that they briefly emit light successively in time.

The marker arrangement 5 also comprises three LEDs 51 with a direct line of sight 5d to the cameras 31, 32, so that the position of the marker arrangement 5, and hence the position of the vertebra 17, can also be determined.

In order to enable positions to be determined also when the surgical instrument 4 occupies the position 6 denoted by dashed lines, or when the direct lines of sight 4d, 5d have to be blocked, for example by attending staff or other apparatus, a mirror 7 is arranged above the patient, for example rigidly mounted on the ceiling; via this mirror indirect lines of sight 6i and 5i can be established between the LEDs of the surgical instrument 6 or the marker arrangement 5 and the cameras 31, 32, respectively. To this end, the marker arrangement 5 is also provided with markers 52 (three LEDs) on the side facing the mirror 7. In order to determine the position of the surgical instrument 6 or the marker arrangement 5, the cameras 31, 32 measure the virtual light points of the LEDs in the mirror 7; these points are subsequently converted, using a suitable evaluation electronic circuit, into the actual position and orientation of the surgical instrument 6 or the marker arrangement 5 (and the vertebra 17). To this end, the exact position and orientation of the mirror 7 must be known. This position and orientation can be measured, for example in advance or instantaneously by means of a marker arrangement 8 which is provided on the mirror 7 and has a direct line of sight to the cameras 31, 32.

For example, on the basis of the spatial region in which the light dots are detected by the cameras 31, 32 it can be detected whether at the relevant instant a virtual light position in the mirror 7 or an actual light position of a LED is determined. Another possibility would consist in sequentially controlling the LEDs on the mirror 7, on the instrument 4 or 6, and on the marker arrangement, so that the association is defined.

If the position of the virtual light dot associated with the same LED as well as the position of the actual light point was determined, for example using a suitable algorithm the actual position could be verified by means of the position determined from the virtual light point so that possibly the measuring accuracy could be increased.

The detector arrangement 3 is connected to a control and evaluation unit 10 via a data and control lead 16. This unit includes notably an arithmetic unit 11 for evaluating the position data measured by the cameras 31, 32 and for determining the actual positions, an image storage unit 12 for storing previously determined image data, and an image processing unit 13 for determining an image in which the current position of the surgical instrument 4 and the marker arrangement 5 (or the vertebra 17) is always reproduced. Such an image can always be instantaneously displayed on a monitor 14 during the treatment; for example a surgical instrument 15 is reproduced in the image.

The described stationary arrangement of the mirror provided with LEDs offers the advantage that the detector arrangement can always be moved at random in space and be newly calibrated, i.e. its position in space relative to the LEDs of the mirror can be determined again at any time. However, other arrangements of the mirror are also feasible. It is also possible to provide several mirrors so as to increase the field of view of the detector arrangement even further, resulting in an even higher operating reliability.

The specific construction of the detector arrangement and the marker arrangement does not have a special effect on the invention. Instead of the two line cameras shown, use can be made of three cameras, each of which determines a one-dimensional position. The number and the type of markers used for the marker arrangement may also be different (for example, more than three LEDs per marker arrangement; markers with an identification pattern which is recognized by a suitable camera or another detection device in order to determine its position therefrom).

All references cited herein are incorporated herein by reference in their entirety and for all purposes to the same extent as if each individual publication or patent or patent application was specifically and individually indicated to be incorporated by reference in its entirety for all purposes.

What is claimed is:

1. An optical position measuring system for an image-guided surgery system, comprising:

a first marker arrangement;

a detector arrangement for optically determining the position of the first marker arrangement, the detector arrangement normally having an unblocked first line of sight to the first marker arrangement; and a mirror for establishing an alternative second line of sight between the detector arrangement and the first marker arrangement for providing an alternative optical path between the first marker arrangement and the detector arrangement when the first line of sight is blocked.

2. A system as claimed in claim 1 further comprising a second marker arrangement on the mirror provided in order to determine the position and orientation of the mirror.

3. A system as claimed in claim 1 wherein the first marker arrangement comprises a plurality of markers which are arranged in such manner that a direct as well as an indirect line of sight exists to the detector arrangement.

4. A system as claimed in claim 1 further comprising means for associating a marker signal detected by the detector arrangement with one of the first and second marker arrangements.

5. A system as claimed in claim 4 wherein the first and the second marker arrangements have a different construction.

6. A system as claimed in claim 4 wherein the first and the second marker arrangements are controlled successively in time.

* * * * *